(12) United States Patent
Moorty et al.

(10) Patent No.: US 6,733,802 B1
(45) Date of Patent: May 11, 2004

(54) NATURAL AZADIRACHTIN COMPOSITION

(75) Inventors: Sistla Ramchandra Moorty, Secunderbad (IN); Annam Dilip Kumar, Secunderbad (IN)

(73) Assignee: Fortune Bio-Tech Limited, Secunderbad (IN)

( * ) Notice: Subject to any disclaimer, the term of this patent is extended or adjusted under 35 U.S.C. 154(b) by 19 days.

(21) Appl. No.: 09/808,970

(22) Filed: Mar. 16, 2001

Related U.S. Application Data

(63) Continuation of application No. 09/746,546, filed on Dec. 11, 2000, which is a continuation of application No. 08/992,515, filed on Dec. 17, 1997, now abandoned.

(51) Int. Cl.$^7$ .............................................. A61K 35/78
(52) U.S. Cl. ...................................... 424/761; 424/756
(58) Field of Search ................................ 424/761, 756

(56) References Cited

U.S. PATENT DOCUMENTS

| | | | |
|---|---|---|---|
| 4,058,067 A | 11/1977 | Wright et al. | |
| 4,556,562 A | 12/1985 | Larson | |
| 5,001,146 A | 3/1991 | Carter et al. | |
| 5,110,591 A | 5/1992 | Williams | |
| 5,124,349 A | 6/1992 | Carter et al. | |
| 5,281,618 A | 1/1994 | Walter | |
| 5,298,247 A | 3/1994 | Godrej et al. | |
| 5,298,251 A | 3/1994 | Locke et al. | |
| 5,352,672 A | 10/1994 | Staetz et al. | |
| 5,352,697 A | 10/1994 | Butler et al. | |
| 5,356,628 A | 10/1994 | Locke et al. | |
| 5,368,856 A | 11/1994 | Locke et al. | |
| 5,372,817 A | 12/1994 | Locke et al. | |
| 5,391,779 A | 2/1995 | Lidert | |
| 5,395,951 A | 3/1995 | Nagasampagi et al. | |
| 5,397,571 A | 3/1995 | Roland et al. | |
| 5,503,766 A | * 4/1996 | Kulperger | 252/174.12 |
| 5,635,193 A | 6/1997 | Walter et al. | |
| 5,695,763 A | 12/1997 | Kleeberg | |
| 5,707,638 A | 1/1998 | Lösel et al. | |
| 5,827,521 A | 10/1998 | Moorty et al. | |
| 5,839,224 A | 11/1998 | Emerson et al. | |
| 5,856,526 A | 1/1999 | Sankaram et al. | |
| 5,939,441 A | * 8/1999 | Stetter et al. | 514/341 |

FOREIGN PATENT DOCUMENTS

| | | |
|---|---|---|
| AU | 1122088 | 1/1989 |
| CA | 2013754 | 6/1991 |
| CA | 2188110 | 4/1997 |
| CN | 1039249 | 1/1990 |
| EP | 0538246 | 4/1993 |
| GB | 2113092 | 8/1983 |
| GB | 2259857 | 3/1993 |
| JP | 5225032 | 2/1977 |
| JP | 59155398 | 9/1984 |
| WO | 9219616 | 11/1992 |
| WO | 9510184 | 4/1995 |
| WO | 9628023 | 9/1996 |

OTHER PUBLICATIONS

Nakayama et al., Chem. Pharm Bull (Tokyo) 34(5): 2209–2213 (1986). Abstract.*
Liang et al., J. Am. Chem. Soc. 57 :525–527 (1935). Abstract.*
Jitoe et al., J. Agric. Food Chem. 40(8): 1337–1340 (1992). Abstract.*
Sundaram et al., "Part B–Pesticides Food Contaminants and Agricultural Wastes" *J Environ Sci and Health* (1996) 31(5):1041–60.
Ladd et al., *J. Econ Entomo* (1984) 77:903–05.
Hirahara et al., *Eiyogaku Basshi* (1974) 32(1):1–8.
Hong et al., *J Korean Agric Chem Soc* (1990) 33(2):143–6.
Balandrin et al., *Science* (1985) 228(4704):1154–60.
Jain et al., *Phytother Res* (1991) 5(3):139–41.
Tilak BD., Crop Protection Agents–Their Biological Evaluation. (McFarlan NR., ed), (1977), pp. 99–109, Academic Press, London.
Dohroo et al., *Agric Rev* (1995) 16(3):133–40.
Schroeder and Nakanishi, *J Natural Prod.* (1987) 50(2):241–44.
Feuerhake and Schmutterer, *J Plant Dis Protect* (1982) 89(12):737–47.
Wan et al., *Bull Environ Contam Toxicol* (1996) 56(3):432–9.

* cited by examiner

*Primary Examiner*—Jean C. Witz
(74) *Attorney, Agent, or Firm*—Gray Cary LLP; Dean Nakamura

(57) ABSTRACT

A natural, plant-derived insecticidal formulation is described.

20 Claims, No Drawings

NATURAL AZADIRACHTIN COMPOSITION

This application is a Continuation of 09/746,546, filed Dec. 11, 2000, which is a Continuation of 08/992,515 filed Dec. 17,1997 now abandoned.

The instant invention relates to insecticidal formulations containing solely naturally occurring, plant-derived active agents and reagents.

BACKGROUND OF THE INVENTION

Many insecticidal formulations are available, some containing naturally occurring insecticidal active agents, or derivatives thereof, such as azadirachtin.

However, those formulations invariably contain synthetic active agents, synthetic inert ingredients and/or long-lived or toxic organic solvents. Also, many of the extraction methods to obtain a naturally occurring insecticidal agent rely on such synthetic reagents. Hence, solvent residues and residual amounts of those synthetic solvents and reagents remain in the extract.

All of those synthetic reagents contribute to the overall toxicity of the formulation. Many of the formulation ingredients have a detrimental environmental effect.

SUMMARY OF THE INVENTION

An object of the instant invention is to provide an insecticidal formulation made solely of naturally occurring, plant-derived, biodegradable ingredients.

Another object is to provide a formulation of high azadirachtin content, free from aflatoxins and synthetic solvents, surfactants, stabilizers and the like commonly used in pesticidal formulations.

Those and other objects have been attained in the discovery and development of naturally occurring reagents for use in an azadirachtin insecticidal formulation, wherein the components generally are plant-derived and are biodegradable, and are prepared in a manner wherein the amount of synthetic reagents found in the final formulation can be essentially zero.

DETAILED DESCRIPTION OF INVENTION

As used herein, "natural", is meant to indicate that a compound is found in nature. Generally, that natural compound is "plant-derived", that is, obtained from a plant, and is biodegradable. That is to distinguish a reagent of interest from one which is made synthetic, that is, a compound which is man-made, or one with a negative environmental effect. The instant reagents and compositions of interest generally are devoid of such synthetic reagents, as determined using known diagnostic assays or bioassays, such that a synthetic is present at levels below the normal level of detection for the method used or the level of synthetic is not statistically different from the determined background level.

The insecticidal active agent of interest is a naturally occurring compound such as azadirachtin. Preferably, the extracted azadirachtin is in solid form. The purity of the solid azadirachtin can vary but compositions of high purity are desirable. The final formulation of interest can be a product having about 15% azadirachtin, possibly about 10%, about 5% or even about 2% or 1% active agent. (Unless indicated otherwise, percentages are provided in terms of a w/w relationship, generally in terms of the final composition.) Formulations having as little as about 0.2% active agent are effective. The concentration of the active agent will depend on whether the product is a concentrate for dilution by the end user or is a formulation ready for application without any further manipulation.

Methods for obtaining a solid azadirachtin composition are known and the artisan is directed to, for example Shroeder & Nakanishi, J. Nat. Prod. 50:241–284, 1987; "Neem-A Tree for Solving Global Problems" National Academy Press, Washington, D.C., 1992; U.S. Pat. No. 5,001,146; and U.S. Pat. No. 4,946,681.

A suitable process for extracting azadirachtin is one in which the product contains about 10%–25% azadirachtin, which can be purified further to a level of 40% or greater. The product containing 10%–25% azadirachtin can be identified as, "technical", azadirachtin.

Another feature of the instant invention is a process for obtaining a surface active agent from certain plants. That surface active agent can be identified under a variety of different names, such as emulsifier, surfactant or detergent. The basic principle behind the plant-derived surface active agent of interest is that said agent reduces surface tension when dissolved in an aqueous medium or which reduces interfacial tension between two liquids or between a liquid and a solid. Emulsifiers, detergents and surfactants are operate on that same basic chemical mechanism, the nomenclature varies chiefly in the nature of the surfaces involved. Another acceptable term is a colloid.

For example, saponins, a plant glycoside which on shaking with water forms colloidal solutions giving soapy lathers, and sapogenins are suitable plant-derived surface active agents which are useable in the practice of the instant invention. The saponins commonly are grouped into two categories, the triterpenoid and the steroid saponins. Either can be used in the practice of the instant invention.

The plant parts, and particularly the fruit of a plant of the genus of Saponaria, Quillaja, Chlorogalum and Sapindus, commonly known as soapnut, can be used to obtain suitable surface active agents.

Also, known compounds with an emulsifying activity, such as lecithin, and other amphipathic compounds can be used in the practice of the instant invention. A suitable source of lecithin is soy beans.

Surface active agents not of plant origin can be used in the practice of the instant invention. A number of suitable surface active agents which are commercially available can be used. For example, those compounds known as Tritons (various polyoxyethylene ethers), Tweens (various polyoxyethylenesorbitans), Brij's (various polyoxyethylene ethers) and Spans (various sorbitan esters) can find use in the instant invention. Those surface active agents do not have a negative environmental impact at the levels used in the instant invention.

At least about 10% of the final formulation comprises a surface active agent, however, that amount can be increased depending on the product, whether a concentrate or an end use product. Thus, the concentration of surface active agent can approach about 50% by weight of the final product. A preferred amount in a concentrate is about 25% to about 20% to about 15%. Either a single species of surface active agent or a plurality of surface active agents can be used so long as the aggregate amounts abide by the amounts recited hereinabove.

Some of the surface active agents of interest for use in the instant invention are the saponins and sapogenins of various plants. They can be obtained from, for example, the fruit of, for example, Sapindus trifoliatus. Dried fruits of Sapindus trifoliatus are decorticated and the seed removed. The rind is pulverized to yield a coarse powder. The coarse powder is extracted with a lower alcohol, such as methanol, ethanol, isopropyl alcohol and the like, preferably the alcohol is a C1–C5 monohydroxylated alcohol. Isopropyl alcohol is a preferred alcohol. A ratio of about 1:2.5 by weight of coarse powder to alcohol is maintained.

The mixture is agitated and maintained at temperature of about 70–75° C. over a period of about 4 hours to extract the surface active agents. The mixture is cooled to ambient temperature and the solids and liquids are separated by filtration or any other known means. The liquid phase is collected and concentrated by evaporation or more quickly under vacuum to provide a soapnut concentrate. The resultant concentrate is dried, for example, in a vacuum shelf drier at about 60° C. for about 4 hours. The product obtained is pulverized and stored in air tight containers since it can be hygroscopic and can tend to cake.

The formulation of interest optionally can contain antioxidants. Suitable antioxidants are for example, vitamin C, tocopherols, grape seed oil and so on. A preferred antioxidant is plant-derived. A suitable source of an antioxidant is a plant of the genus Zingiber, such as Zingiber officinale, or a plant of the genus Curcuma, such as, Curcuma longa.

Generally, when used, about 20% of the formulation comprises an antioxidant, but lower amounts, such as about 5%, about 3% and as low as about 0.5% can be used. A suitable amount is about 10%. Moreover, a plurality of antioxidants can be used, so long as the aggregate amounts of antioxidants are as provided hereinabove.

An extract of Curcuma longa and Zingiber officinale can be made by powdering the dry rhizome and extracting with a lower alcohol at about 60° C. for about 6 hours. A suitable alcohol is isopropyl alcohol. The alcohol extract is separated by filtration, the solvent stripped by passing through a falling film evaporator and the concentrates dried in a vacuum drier for about 6 hours. The semisolid extract is stored in air tight containers away from sunlight.

The formulation of interest also can contain a synergist, which may have a ultraviolet light blocking or absorbing activity. A suitable synergist in the practice of the instant invention is a vegetable oil, such as those from sesame, rape or sunflower.

A suitable amount of the synergist is from about 10% to about 15%.

An essential oil for dissolving the active agent, azadirachtin, can be, such as those derived from citronella, lemon grass, geramiol, rusagrass and the like, which are readily available in commercial quantities. An essential oil of interest is a steam distillate of, for example, a grass or other plant.

A suitable amount of essential oil is that amount to obtain the desired concentration of active agent.

The various elements of a formulation of interest can be prepared as two reagents for eventual mixing or as a single reagent.

As to the former, the first reagent contains the active agent dissolved in an essential oil. The active agent can be present in an amount suitable to serve as a reagent. Generally the concentration is higher than that of the final product. Concentrations of up to 50% or more can be used. Generally amounts of about 20% are suitable.

The second of the two reagents is a mixture of one or more surface active agents, a synergist and optionally, one or more antioxidants. The second of the two reagents may be called an emulsification medium.

Thus, a 5% active ingredient composition can be obtained by adding 250 gms of technical azadirachtin of 20% purity to 600 ml of citronella oil. The mixture is stirred for about 30 minutes and filtered to remove insolubles. The preparation is made up to 1 liter with citronella oil.

Separately, the surface active agent is suspended in an aqueous medium, such as water. The surface active agent can be a single species of compound or can be a combination of compounds so long as the total amount of surface active agents does not exceed the amounts recited hereinabove. Following vigorous mixing or by passing the mixture through a colloidal mill to provide a micro-mulsion, the mixture can be filtered. The synergist and any antioxidants are incorporated into the mixture.

Thus, for example, a 20% solution of soapnut extract can be obtained by adding 200 gms of the soapnut extract to 800 ml of water under agitation and stirring for about 30 minutes. Then, optionally, any one or more of the following can be added, about 20 gms of soy lecithin, about 20 gms of Curcuma longa extract and about 20 gms of Zingiber officinale, to the mixture with thorough mixing. Then, 50 gms of vegetable oil (sesame, rape or sunflower, for example) are added and the volume of the mixture is brought up to 1 liter with water. The mixture is passed through a colloidal mill to give a uniform suspension, the emulsification medium.

The one liter emulsification medium and 1 liter of a 5% azadirachtin essential oil solution are added to a suitable quantity of water and stirred well for spraying onto the foliar surface of the plants. The volume of water used is that amount to obtain a suitable dilution of the active agent as needed. For example, about a 1:20 dilution with water is suitable so that a final application amount of azadirachtin of about 10 to about 100 ppm, and more preferably about 20 to about 80 ppm, of azadirachtin is obtained.

Alternatively, all of the essential ingredients can be mixed together as a single reagent. The active agent, one or more surface active agents, synergist, essential oil and optionally one or more antioxidants, are mixed together with a suitable volume of water to provide a stable emulsion.

The instant invention provides the advantage of an insecticidal formulation for use on plants with a minimum of, if any, synthetic, and likely toxic chemicals. Essentially, the entire final formulation can be comprised of plant-derived compounds. A composition of interest devoid of synthetic compounds generally is one wherein the amount of synthetic compounds in a composition of interest generally is less than 5%, preferably, less than 2%, and more desirably, less than 1% of the final formulation. Thus, the instant formulations will find ready use as a "natural" product with a minimum of toxic residues.

The invention will now be described by way of the following non-limiting examples.

EXAMPLES

Example-1

One thousand five hundred kgs of dry soapnut fruit were decorticated and the seeds removed. The pulp was pulverized to a coarse powder (800 kgs). The coarse powder was extracted with isopropyl alcohol (2000 kgs) under agitation and at temperatures between 70–75° C. After 4 hours, the mass was cooled and isopropyl alcohol extract separated by filtration. The isopropyl alcohol extract was processed in a falling film evaporator until about 95% of the liquid was removed. The concentrate was dried in a vacuum shelf drier at 60° C. for four hours. The product was pulverized (225 kgs) and stored in airtight containers.

Example-2

Azadirachtin insecticidal formulations of the instant invention can contain more than 60% essential oil. The emulsification medium of the instant invention contains more than 60% water, more than 20% of Sapindus trifoliatus extract, more than 2% each of extracts of Curcuma longa and Zingiber officinale; more than 5% of vegetable oil, i.e. rape seed, sesame or Sunflower, and more than 10% soy lecithin, all available commercially.

All references cited herein and incorporated herein by reference in entirety.

It should be well appreciated that various changes can be made to the teachings herein without departing from the spirit of the instant invention.

What is claimed:

1. An emulsion comprising a biologically effective amount of azadirachtin in an essential oil, and a surface active agent, wherein said emulsion is made from naturally occurring materials and is devoid of synthetic compounds.

2. The emulsion of claim 1, wherein said biologically effective amount of azadirachtin is from about 0.2% (w/w) to about 15% (w/w).

3. The emulsion of claim 2, wherein said amount of azadirachtin is from about 0.2% (w/w) to about 1% (w/w).

4. The emulsion of claim 2, wherein said amount of azadirachtin is from about 2% (w/w) to about 10% (w/w).

5. The emulsion of claim 4, wherein said amount of azadirachtin is about 5% (w/w).

6. The emulsion of claim 1, wherein said surface active agent is saponin or a sapongenin.

7. The emulsion of claim 1, wherein said surface active agent is obtained from the plant of the genus Saponaria, Quillaja, Chlorogalum, or Sapindus.

8. The emulsion of claim 1, wherein said surface active agent is a lecithin.

9. The emulsion of claim 1, wherein the amount of surface active agent is from about 10% (w/w) to about 50% (w/w).

10. The emulsion of claim 9, wherein said amount of surface active agent is from about 15% (w/w) to about 25% (w/w).

11. The emulsion of claim 10, wherein said amount of surface active agent is about 20% (w/w).

12. The emulsion of claim 1, further comprising an anti-oxidant.

13. The emulsion of claim 12, wherein said anti-oxidant is selected from the group consisting of vitamin C, tocopherol and grape.

14. The emulsion of claim 12, wherein said anti-oxidant is obtained from a plant of the genus Zingiber or Curcuma.

15. The emulsion of claim 12, wherein the amount of anti-oxidant is from about 0.5% (w/w) to about 20% (w/w).

16. The emulsion of claim 15, wherein said amount is about 10% (w/w).

17. The emulsion of claim 1, further comprising an ultraviolet light blocking or absorbing agent.

18. The emulsion of claim 17, wherein said agent is a vegetable oil.

19. The emulsion of claim 17, wherein the amount of said agent is from about 10% (w/w) to about 15% (w/w).

20. An insecticidal composition comprising a naturally occurring azadirachtin and an essential oil and an emulsification medium comprising a naturally occurring surface active agent and a naturally occurring ultraviolet light blocking or absorbing agent.

* * * * *